(12) United States Patent
Palatinus et al.

(10) Patent No.: US 12,072,305 B2
(45) Date of Patent: Aug. 27, 2024

(54) METHODS FOR DETERMINING CRYSTAL STRUCTURE AND APPARATUS FOR CARRYING OUT THE METHODS

(71) Applicant: Fyzikálníústav AV ČR, v. v. i., Prague (CZ)

(72) Inventors: Lukas Palatinus, Prague (CZ); Petr Brazda, Prague (CZ); Paul Benjamin Klar, Prague (CZ)

(73) Assignee: FYZIKALNI USTAV AV CR. V.V.I, Prague (CZ)

( * ) Notice: Subject to any disclaimer, the term of this patent is extended or adjusted under 35 U.S.C. 154(b) by 0 days.

(21) Appl. No.: 17/565,624

(22) Filed: Dec. 30, 2021

(65) Prior Publication Data

US 2023/0065841 A1    Mar. 2, 2023

(30) Foreign Application Priority Data

Sep. 1, 2021 (CZ) .................... CZ2021-403

(51) Int. Cl.
*G01N 23/2055* (2018.01)
*G01N 23/20058* (2018.01)

(52) U.S. Cl.
CPC .... *G01N 23/20058* (2013.01); *G01N 23/2055* (2013.01); *G01N 2223/0566* (2013.01)

(58) Field of Classification Search
CPC ......... G01N 23/20058; G01N 23/2055; G01N 2223/0566; G16C 20/20
See application file for complete search history.

(56) References Cited

U.S. PATENT DOCUMENTS

2024/0077436 A1* 3/2024 Vespucci .......... G01N 23/20058

* cited by examiner

Primary Examiner — Jurie Yun
(74) Attorney, Agent, or Firm — Michael D. Eisenberg (57) ABSTRACT

The present invention relates to a method for determining the crystal structure of a crystal (4) capable of electron diffraction. The method includes the steps of obtaining a three-dimensional electron diffraction pattern and processing data from the electron diffraction pattern. The essence of the invention is that the method of determination consists in creating virtual diffraction frames containing a list of integrated scattered electron intensities. Subsequently, the dynamical diffraction theory is used in the data processing step. In another embodiment, the invention provides an apparatus capable of performing this method.

15 Claims, 4 Drawing Sheets

METHODS FOR DETERMINING CRYSTAL STRUCTURE AND APPARATUS FOR CARRYING OUT THE METHODS

CROSS REFERENCE TO RELATED APPLICATION

The present application claims priority benefit from CZ2021-403 filed on 1 Sep. 2021 by Fyzikalni ustav AV CR, v.v.i., Prague, Czech Republic.

BACKGROUND OF THE INVENTION

Field of the Invention

The present invention relates to a computer-implemented invention. More particularly, the present invention relates to a processing of rotational electron diffraction data on crystalline substances. In one embodiment, the invention relates to a method of refining a crystalline structure from rotation electron diffraction using dynamical refinement of the data, said method being capable to accurately determine atomic structure.

Description of Related Art

Structure analysis is a method of obtaining information on the spatial arrangement of atoms in a crystal structure. The analysis includes several steps: crystal preparation, data acquisition, finding the initial structure model and optimizing the structure model.

The structure model is optimized by a mathematical procedure called the least squares method. In this procedure, the experimental diffraction data are measured on a crystal and compared with theoretical diffraction data calculated on the basis of a real structure model. The difference between experimental and theoretical data is minimized by adjusting the structure model. For this procedure to be successful, the calculation of theoretical data from the structure model must be accurate.

If electrons are used in the data acquisition step, it is known as an electron diffraction experiment. In this case, the calculation of theoretical diffraction intensities is a complicated method. The reason is the presence of so-called "dynamical diffraction effects".

The method of calculation of accurate theoretical diffraction data, so-called refinement, from electron diffraction was designed for a special case of precession electron diffraction data. A comparable method has not yet been available for general electron diffraction data.

The object of the present invention, in view of the above-mentioned disadvantages, is to provide a method of refining the crystal structure, the steps of which are performed by a computer so that the method is suitable for obtaining good structure optimization with general electron diffraction data, i.e. not only for the special case of precession electron diffraction.

Further object of the present invention is to provide a computer-implemented method using a wide range of crystallographic calculations and also able to determine the electrostatic potential distribution and crystal structure for a wide range of compounds and crystal types.

BRIEF SUMMARY OF THE INVENTION

In a first aspect of the present invention, a method for determining a crystal structure model is provided. The method preferably includes, but it is not limited to, organic crystals. Crystal structure determination can be performed on inorganic crystals, such as metal-comprising compounds, e.g. hydrated cobalt and aluminum phosphate, or minerals, such as quartz, natrolite, as well as on organic crystals, e.g. amino acids, hydrocarbons and their derivatives, and a number of drugs, such as abiraterone acetate. Particular advantage is, however, achieved on protein structure determination, crystalline structure determination on antibodies, gene and drug delivery samples.

The method comprises the steps:

obtaining electron diffraction data from the crystal by three-dimensional electron diffraction, wherein the data comprising information on the crystal diffraction patterns, wherein each diffraction pattern comprising information on the scattered electron intensities in each direction and the crystal orientation to the incident electron beam during data acquisition, wherein the crystal is rotating or tilting during recording of the diffraction data;

processing the data determining crystal lattice parameters, crystal orientation at the time of the diffraction pattern acquisition, indices of each reflection and the scattered electron intensity of each reflection on each diffraction pattern, thereby producing the processed data;

generating virtual diffraction frames by a computer program, wherein each virtual diffraction frame comprising a list of integrated scattered electron intensities for each direction with summed contributions from all experimental patterns forming one virtual frame, the virtual diffraction frames being formed by calculation from the provided three-dimensional electron diffraction data;

providing an approximate crystal structure model; and refining the approximate crystal structure model using dynamical diffraction theory, wherein the refining comprising steps:

calculating modeled intensities of scattered electrons using dynamical diffraction theory based on the approximate crystal structure model; and minimizing the difference between experimentally determined scattered electron intensities and modeled intensities, wherein the refined crystal structure model is the model with the smallest deviation.

The method according to the invention is capable to determine crystal structure, preferably an absolute structure of a non-centrosymmetric crystal, which can be obtained by dynamical refinement. In comparison with the kinematic approximation, the method according to the present invention does not ignore the dynamic diffractive effects in the diffraction data, and therefore allows to obtain more accurate information about the crystal structure. The combination of the steps according to the method of the present invention is adapted to create a so-called virtual diffraction frame, wherein theoretical data corresponding to experimental data in the virtual diffraction frame which can be more easily calculated from the crystal structure model, compared to the prior art methods in which virtual diffraction frames are not created. As a result, structure models can be obtained with an accuracy similar to the model established by precession electron diffraction and much better than the procedures currently used for non-precession electron diffraction data. The advantage of the method using non-precession data over precession data is their easier availability without requiring special equipment for the precession method, faster data processing and lower overall illumination of the electron crystal during data acquisition, which is advantageous especially in the analysis of organic materials sensitive to electron irradiation. Such an optimized structure model provides better insight into crystal structures and thus provides essential information, such as the absolute structure of crystals with chiral molecules or the positions of light atoms, which are difficult to detect but are often crucial for the function and use of the material.

In a preferred embodiment, the method for determination an absolute structure of a non-centrosymmetric crystals is provided. The method further comprises steps:
creating a model of opposite absolute structure to the current approximate crystal structure model, thereby creating an inverted model;
refining the approximate crystal structure model using dynamical diffraction theory on the inverted model; and
comparing quality indicators of the inverted model, wherein the correct structure is the one that leads to the smallest deviation between the experimental data and the data calculated on the basis of the refined structure model.

In a second aspect of the present invention, a further method for determining the absolute structure of a non-centrosymmetric crystal, wherein the crystal is capable of electron diffraction, is hereby disclosed. The method comprises the steps:
obtaining electron diffraction data from the crystal by three-dimensional electron diffraction, wherein the data comprising information on the crystal diffraction patterns, wherein each diffraction pattern comprising information on the scattered electron intensities in each direction and the crystal orientation to the incident electron beam during data acquisition, wherein the crystal is rotating or tilting during data acquisition; and
processing the data determining crystal lattice parameters, crystal orientation at the time of the diffraction pattern acquisition, indices of each reflection and the scattered electron intensity of each reflection on each diffraction pattern, thereby producing the processed data;
generating virtual diffraction frames by a computer program, wherein each virtual diffraction frame comprising a list of integrated scattered electron intensities for each direction with summed contributions from all experimental patterns forming one virtual frame, the virtual diffraction frames being formed by calculation from the provided three-dimensional electron diffraction data;
providing an approximate crystal structure model;
calculating quality indicators of the approximate crystal structure model using the dynamical diffraction theory to calculate the model intensities;
creating a model of opposite absolute structure to the current approximate crystal structure model, thereby creating an inverted model;
calculating quality indicators of the inverted crystal structure model using the dynamical diffraction theory to calculate the model intensities; and
comparing quality indicators of the inverted and non-inverted models, wherein the correct structure is the one that leads to the smallest deviation between the experimental data and the data calculated on the basis of the refined structure model.

Rotation in steps or continuously means that the sample rotates around the axis of rotation in a certain preselected range, e.g. from −50° to 50°, either in individual defined steps, e.g. 1°, or continuously. The diffraction pattern is exposed in a "step" mode either after each rotation, in a continuous mode during crystal rotation, see, for example, Gemmi M, Mugnaioli E, Gorelik T E, Kolb U, Palatinus L, Boullay P, et al. *3D Electron Diffraction: The Nanocrystallography Revolution. ACS Cent Sci.* 2019 Aug. 28; 5 (8): 1315-29.

The diffraction pattern is a record of the directions and intensities of electrons scattered by a crystal, usually obtained by an electronic device—an electron detector, placed so that the crystal is located between the electron source and the detector. Diffraction acquisition takes the form of image, i.e. two-dimensional record and contains information about the intensity of reflections. A typical example of diffraction acquisition can be seen in FIG. 1.

The skilled person in the art understands the reflection as a place of impact of the diffracted beam on the detector, see e.g. the textbook Václav Valvoda, Milena Polcarová, Pavel Lukáč, Základy strukturni analýzy, Karolinum, Prague, 1992, ISBN 80-200-0280-4.

An approximate crystal structure model is understood to be a list of atoms with their approximate positions in the basic cell of the crystal and with the determination of the atom type. This model can be obtained either from the literature, if it has already been published, or directly from diffraction data by established methods of structure analysis, see. e.g. textbook Giacovazzo, C. (editor), *Fundamentals of Crystallography, Third Edition*, Oxford University Press, 2011, ISBN 9780199573653. In another embodiment, the skilled person may provide pre-analysis of the data obtained from the experimental diffraction pattern and provide an educated estimation of the approximate crystal structure model.

The necessary information obtained from the diffraction data are the parameters of the unit cell of the crystal, also known as crystal lattice parameters, and the list of scattered electron intensities and their standard deviations of all reflections measured during the experiment. The reflections are characterized by three (in exceptional cases more than three) integer indices determining their position in the reciprocal crystal lattice, see e.g. the textbook Václav Valvoda, Milena Polcarová, Pavel Luksáč, Základy strukturni analýzy, Karolinum, Prague, 1992, ISBN 80-200-0280-4.

The refinement quality indicator is a numerical value estimating how good and reliable the refined structure model is. This quality indicator can advantageously be the R-factor $R_1$, $R_2$ and $wR_2$ defined as:

$$R_1 = \frac{\sum |\sqrt{I_g^o} - \sqrt{I_g^c}|}{\sum \sqrt{I_g^o}}$$

$$R_2 = \frac{\sum |I_g^o - I_g^c|}{\sum I_g^o}$$

$$wR_2 = \sqrt{\frac{\sum w_g (I_g^o - I_g^c)^2}{\sum w_g I_g^{o2}}},$$

where
$I_g^o$, resp. $I_g^c$ are observed, resp. the calculated intensities of a particular diffracted electron beam characterized by the diffraction vector g, wherein $w = \sigma^{-2}(I_g^o)$ and $\sigma(I_g^o)$ is the standard deviation of the determination $I_g^o$. The particular choice of quality indicator used depends on the application and can be made by the user of the invention on the basis of his expert knowledge.

The present invention is particularly suitable for determining the absolute structure of crystals containing light atoms, such as hydrogen, lithium, beryllium or boron.

A further advantage of the present invention is the ability to achieve precise atomic positions in the structure with an average error below 0.005 nm.

Three-dimensional electron diffraction is a method of data acquisition, especially the intensities of electrons scattered on a studied crystal, with the electron beam and the crystal rotating relative to each other. The rotation can be ensured by rotating the electron beam by means of magnetic coils in a transmission electron microscope or by rotating the crystal by means of a goniometer, or a combination of both methods. In some embodiments, the rotating can be tilting.

In a preferred embodiment of the rotational diffraction data acquisition method, the electron scattering intensities are recorded on a series of consecutive images, with the crystal being rotated by an angle about the goniometer axis after each diffraction pattern acquisition. The magnitude of the rotation is typically between 0.1° and 1°. The total tilt of the crystal can be in the range of typically ±60°, in some embodiment even more.

In a preferred embodiment, the step of obtaining rotating electron diffraction data is a combination of electron beam rotation and crystal tilt, with several diffraction patterns for different electron beam tilts being recorded for each crystal tilt. The preferred embodiment thus has the advantage of greater accuracy in the mutual orientation of the crystal and the beam due to the fact that the inclination of the electron beam can in some cases be controlled with greater accuracy than the inclination of the goniometer.

In another preferred embodiment, continuous crystal tilt is combined with continuous diffraction data acquisition. The crystal goniometer rotates continuously around the tilt axis during electron diffraction imaging. Each image of the rotating electron diffraction covers an angular range, which is determined by the speed of rotation of the goniometer and the exposure time. Unlike sequential rotation, continuous rotation records integrated electron diffraction intensities. This preferred embodiment using a continuous tilt of the crystal offers the advantage of a simpler experimental design, minimizing electron illumination of the crystal and obtaining integrated intensities.

All of the above-described methods of data acquisition by the rotational electron diffraction method are described in detail in M. Gemmi and A. Lanza: 3D *electron diffraction techniques, Acta Crystallographica B*, Vol. 75, pp. 495-504, year of publication 2019.

Data processing comprises the following steps:
finding maxima in all diffraction patterns and determining their coordinates in reciprocal space;
finding parameters of the crystal lattice and determining the orientation of the crystal in space, i.e. determining the so-called orientation matrix;
determination of diffraction intensities of all potentially excited reciprocal lattice points on all diffraction patterns;
A so-called virtual diffraction frame is created as follows:
the appropriate number of consecutive experimental diffraction patterns is selected to be combined into one virtual frame. A suitable number is such that the total angular range covered by the virtual diffraction frame is preferably approximately 1°-3°.
all points of the reciprocal lattice are found that are within the angular range covered by the virtual diffraction frame.
for each found point, all diffraction intensities belonging to the point on all experimental diffraction patterns, are summed.
the list of obtained intensities belonging to the points of the reciprocal lattice forms a data set called the virtual diffraction frame.
the orientation of the virtual diffraction frame is determined as the average of the orientations of all experimental diffraction patterns that make it up.
the angular difference between the following virtual diffraction frames is preferably chosen so that the volumes of the reciprocal space covered by the adjacent virtual diffraction frames partially overlap.

In a preferred embodiment, the data processing also includes a refinement of the diffraction geometry, i.e. a refinement of the orientation of the crystal with respect to the incident electron beam.

Refinement is a general term used to describe all the operations required to develop a test model into a model which best corresponds to the observed data, in particular the intensities of the electrons scattered by the crystal. The refinement can be considered as a sequence of mathematical procedures performed by a computer. The refinement of the crystal structure estimation of the present invention utilizes dynamical diffraction theory, considering the multiple scattering of electrons by atoms in the crystal.

The step of determining the quality of the refined crystal structure model is to determine the deviation, preferably by means of the parameter R, between the observed quantities and the simulated quantities according to the crystal structure model. In the event that a deviation is small enough, the crystal structure model is considered accurate.

In another embodiment of the present invention, an apparatus suitable for determining a crystal structure model according to the present invention is described.

The apparatus comprises:
an electron source capable of emitting an electron beam;
a crystal holder adapted to perform a rotational or tiling movement with the crystal;
a detector detecting electrons scattered from the crystal, the detector is connected to
a data storage and processing unit, wherein
the processing unit is adapted to determine crystal lattice parameters, crystal orientation at the time of the diffraction pattern acquisition, indices of each reflection and the scattered electron intensity of each reflection on each diffraction pattern, thereby producing the processed data; and
generating virtual diffraction frames by a computer program, wherein each virtual diffraction frame comprising a list of integrated scattered electron intensities for each direction with summed contributions from all experimental patterns forming one virtual frame, the virtual diffraction frames being formed by calculation from the provided three-dimensional electron diffraction data; and wherein
the data storage is configured to provide an approximate crystal structure model or the processing unit is adapted to perform analysis of the processed data leading to obtaining an approximate structure model; and wherein
the processing unit is adapted to refine the structure model.

In a preferred embodiment the processing unit is adapted to refine the approximate crystal structure model using dynamical diffraction theory, wherein the processing unit, during the refining, is adapted to:

calculate modeled intensities of scattered electrons using dynamical diffraction theory based on the approximate crystal structure model; and minimize the difference between experimentally determined scattered electron intensities and modeled intensities, wherein the refined crystal structure model is the model with the smallest deviation.

In another preferred embodiment, the processing unit is configured to determine the absolute structure of the non-centrosymmetric crystals, wherein the processing unit is configured to create a model of opposite absolute structure to the current approximate crystal structure model, thereby creating an inverted model;

refine the inverted crystal structure model using dynamical diffraction theory; and compare quality indicators of the inverted and non-inverted models, wherein the correct structure is the one that leads to the smallest deviation between the experimental data and the data calculated on the basis of the refined structure model.

In another preferred embodiment, wherein the processing unit is adapted to refine the approximate crystal structure model; and wherein the apparatus is adapted to calculate quality indicators of the approximate crystal structure model; and compare the quality indicators, wherein the correct crystal structure is considered as the modeled crystal structure leading to the smallest deviation between the experimental data and the data calculated on the basis of the refined structure model.

In another preferred embodiment, the processing unit is adapted to create a virtual model of opposite crystal structure to the structure of the current approximate crystal structure model, thereby creating an inverted model; and wherein the step of comparing quality indicators is comparing quality indicators of the inverted model and experimental data, wherein the correct structure is the one that leads to the smallest deviation between thereof.

Preferably, the detector is set to collect data simultaneously with the rotation of the crystal.

In another preferred embodiment, the detector is set to collect data step by step during the rotation of the crystal.

BRIEF DESCRIPTION OF DRAWINGS

FIG. 2 is a schematic diagram of the creation of virtual diffraction frames from experimental diffraction patterns. In particular.

FIG. 3 is a basic diagram of an apparatus capable of refinement of the structure according to the invention. FIG. 3 shows a source 1 emitting electrons 2, from which the condenser lens system 3 forms a focused electron beam 4 incident on the crystal sample 5, from which the scattered electrons 6 propagate, which are incident on the detector 7 connected to the computing unit 8 further propagates.

DETAILED DESCRIPTION OF THE INVENTION

The embodiment corresponding to an apparatus for carrying out the methods according to the present invention is explained with reference to FIG. 3.

Figure 3:
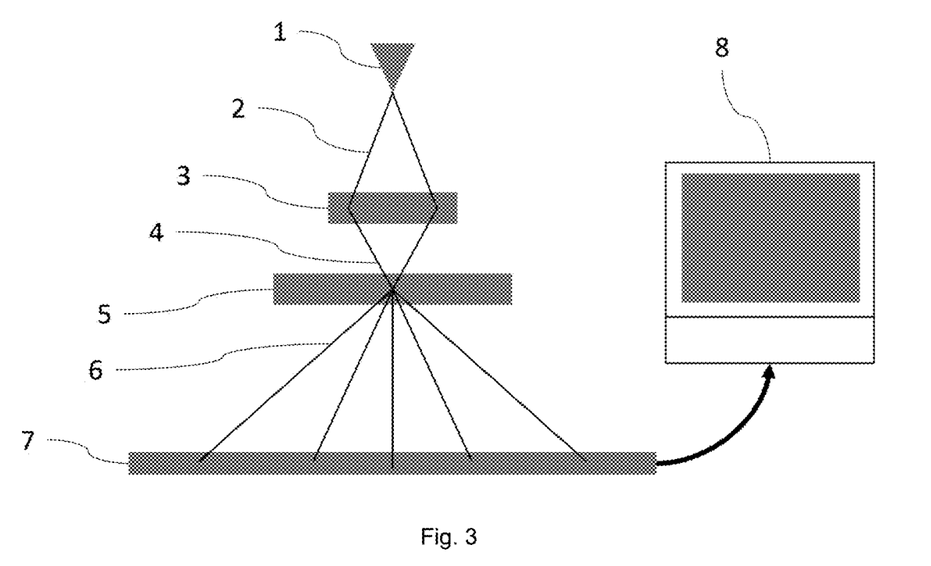

FIG. 3 schematically shows a part of a transmission electron microscope which is further connected to a data storage and processing unit 8 which uses the determination or refinement method according to the present invention. FIG. 3 further shows a transmission electron microscope comprising an electron source 1, which may be, for example, an electron gun. The electron source 1 generates a primary electron beam 2. The electron beam 2 passes through the lens 3 of a system focusing the primary electron beam 2 into the focused electron beam 4, the focused electron beam 4 is directed to the crystal 5 capable of electron diffraction. The source 1 of the primary electrons 2, the lens 3 and preferably also an inclination of the crystal 5 can be controlled by means of a control system. The scattered electrons 6 are detected by a detector 7, which is further connected to a data storage and processing unit 8. The data storage and processing unit 8 further comprises a database and a computer program which processes the data so as to determine and/or refine the crystal structure of the measured crystal 5 by means of the method according to the invention.

In parallel, or subsequently to the measurement step, the computing unit 8 can create an initial inaccurate model of the crystal structure by analyzing the obtained data. In another embodiment, the computer program and the database in the unit 8 may contain information on the estimated crystal 5 structure model from other sources, such as X-ray diffraction. More particularly, the database may further contain information on the crystal structure of crystal 5 determined by X-ray diffraction and/or theoretically predicted models. The structure model of the crystal structure 5 obtained by these methods may be incomplete and/or inaccurate, and the technical problem is therefore to refine this initially inaccurate crystal 5 structure model. The refined crystal 5 structure model can be used to understand the physical and chemical and pharmaceutical properties of the material and thus used generally whenever knowledge of the material's properties is useful or necessary. The use of rotation electron diffraction brings advantages over precession electron diffraction, especially in a simpler experimental setup, cheaper experimental equipment and simpler process of the experiment itself. Thanks to the speed of data acquisition and the efficient use of the electron dose, rotation electron diffraction is also better suited for the study of materials that are extremely sensitive to electron irradiation. Dynamical diffraction theory is used to refine the crystal structure of crystal 5. In one embodiment, the Bloch wave method for calculating diffraction intensities can be used to refine the structure estimation using dynamical diffraction theory. This method is described, for example, in the textbook JCH Spence and J M Zuo, *Electron microdiffraction, Plenum press,* 21992, p. 35 and further.

In this way, the intensity of the scattered electrons 6 is determined according to a given model of the crystal structure of the crystal 5. Alternatively, a multislice method, results of which are equivalent to the Bloch wave method, can be used to calculate the diffracted intensities using the dynamical diffraction theory. The multislice method is described in more detail, for example, in the textbook DB Williams and CB Carter, *Transmission Electron Microscopy, 2nd Edition, Springer,* 2009, p. 533 et seq.

The calculated intensity values are then compared with the measured data, particularly with the scattered electron intensities 6.

The calculated Intensities $I_g^c$ in the rotation data acquisition in a certain embodiment can be obtained by integrating all the calculated intensities at each possible orientation of the crystal 5 into one virtual diffraction frame. The integration can be performed numerically as the sum of the intensities calculated at the finite number of crystal orientations 5.

The refinement of the structure then consists mainly in determining the structure parameters, such as the positions of the atoms, the types of atoms and their scattering parameters. These parameters are varied to minimize the difference between the calculated intensities and the experimental intensities. The calculation may also include parameters related to the crystal and its orientation, i.e. the thickness of the crystal 5 and the mutual orientation of the primary electron beam 4 and the crystal 5. The calculation is also affected by the parameters influencing the calculation of model intensities $I_g^c$.

The least squares method can be used to refine the crystal structure model of crystal 5. In one embodiment, the standard Gauss-Newton algorithm can be used. This approach is sufficient for small residual problems where the starting point is close to the solution, i.e. the model is almost accurate.

The step of determining the quality of the refined model comprising the step of verifying the correspondence of the refined model of the crystal structure with the observed quantities using the refinement quality indicators. In one embodiment, the validation of the crystal structure model can be assessed using one and/or the entire set of refinement quality indicators. The following applies to these indicators:

$$R_1 = \frac{\sum |\sqrt{I_g^o} - \sqrt{I_g^c}|}{\sum \sqrt{I_g^o}}$$

$$R_2 = \frac{\sum |I_g^o - I_g^c|}{\sum I_g^o}$$

$$wR_2 = \sqrt{\frac{\sum w_g (I_g^o - I_g^c)^2}{\sum w_g I_g^{o2}}},$$

wherein
$I_g^o$, resp. $I_g^c$ are observed, resp. the calculated intensities of a particular diffracted electron beam 5 characterized by the diffraction vector g, where $w = \sigma^{-2}(I_g^o)$ and $\sigma(I_g^o)$ is the standard deviation of the determination $I_g^o$.

In case the factor $wR_2$ reaches the minimum value, the crystal structure is considered as refined. The R factor is also sensitive in determining the correct absolute crystal structure. By comparing the factor R for the two variants of the absolute structure and choosing the variant with a lower value of R, it is therefore possible to unambiguously determine which of the two variants is correct. This makes it possible to determine the absolute structure of the crystal and, consequently, the absolute configuration of the molecules contained in the crystal.

The present embodiment thus provides a way to determine or refine the crystal structure of crystal with an accuracy typically better than 0.05 Å.

Figure 4:
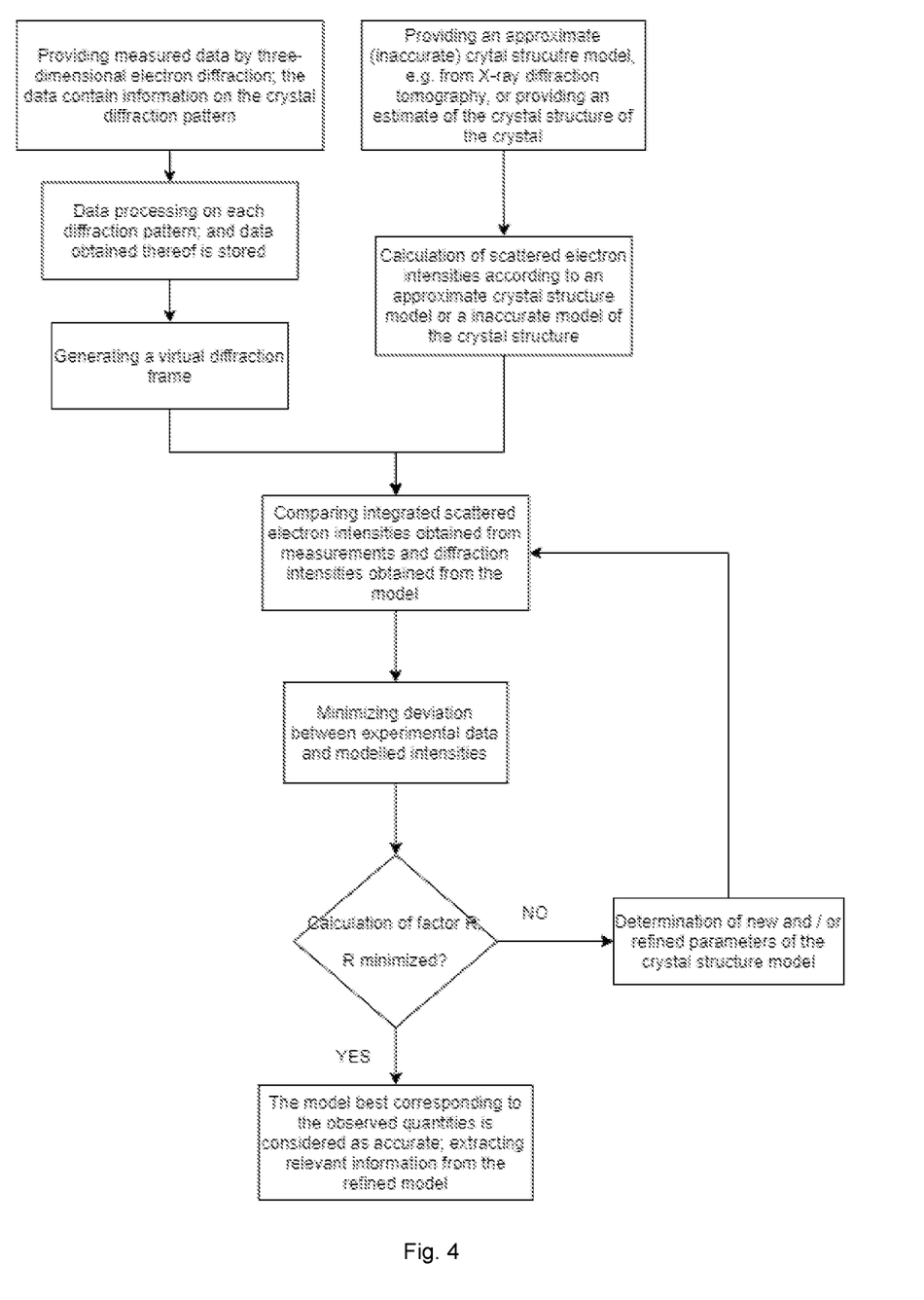
FIG. 4 is a flow chart of a method for refining and/or determining a crystal structure according to the present invention.
Figure 5:
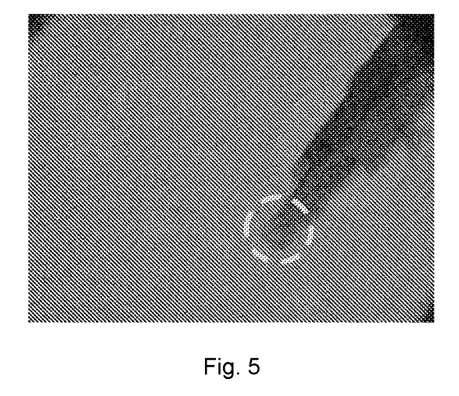
FIG. 5 represents the natrolite crystal used to determine the structure as described in the section Experimental results. The illuminated part is marked with a circle. The diameter of the ring is 750 nm.
Figure 6:
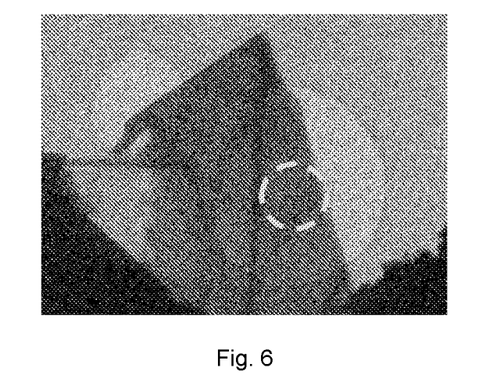
FIG. 6 represents one of the abiraterone acetate crystals used to determine the structure as described in the section Experimental results. The illuminated part is marked with a circle. The diameter of the ring is 850 nm.

The methods according to the present invention are explained in details in mode of operation of the invention which is considered as the best mode. A skilled person in the art may further find useful a general approach shown in FIG. 4.

MODE OF OPERATION OF INVENTION

Experimental Results

The invention has been tested on a number of materials, two of them are listed here—an inorganic crystal of sodium silicate (mineral natrolite) and an organic crystal of abiraterone acetate.

Natrolite

Natrolite is a mineral with the chemical composition $Na_2(Al_2Si_3O_{10})(H_2O)_2$. Its structure has the space group Fdd2, which means that for this material it makes sense to determine the absolute structure.

A sample of natural natrolite from the Mariánská skála, Ústi nad Labem, was crushed into a fine powder in an agate mortar. The powder was applied to a copper grid coated with a carbon membrane. This grid was placed in a sample holder for a transmission electron microscope and placed in a FEI Tecnai G2 20 microscope with an accelerating voltage of 200 kV, with an $LaB_6$ electron source equipped with a SIS Veleta CCD detector.

The acquisition of electron diffraction data from the crystal by the method of three-dimensional electron diffraction took place as follows:

By examining several crystals and visually inspecting their diffraction pattern, a suitable measurement candidate was selected. The crystal goniometer was rotated to the −50° position. The crystal was rotated 0.6° at angular velocity 0.3° per second and its diffraction pattern was recorded on the detector throughout the rotation. The resulting experimental diffraction pattern was saved on a computer hard disk. This diffraction pattern procedure was repeated for another 0.6° rotation. The total rotation of the crystal was 99.6°, so 166 experimental diffraction patterns were obtained in total.

Figure 1:
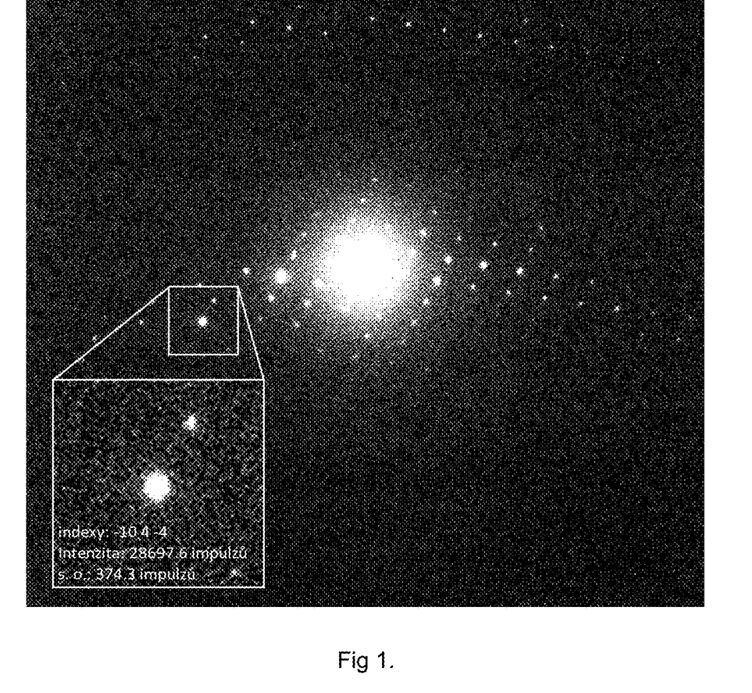
FIG. 1 is an example of a diffraction pattern. The section shows an enlarged image of one reflection with the indicated indexes, intensity and intensity standard deviation.
Figure 2:
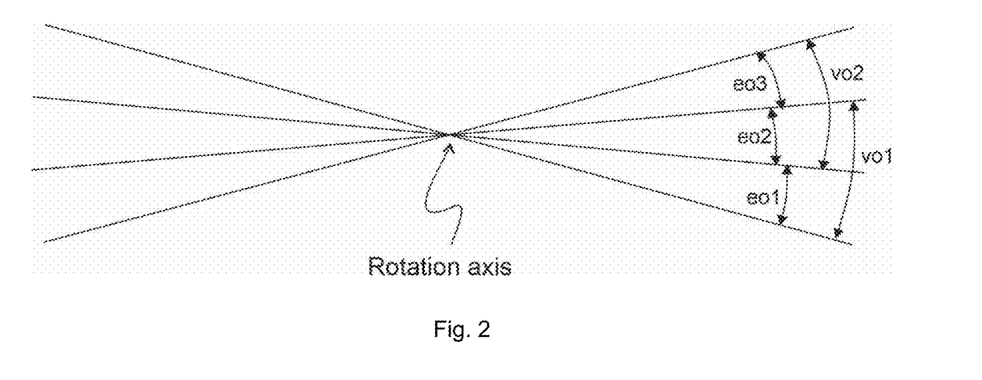
FIG. 2 is a view along the axis of rotation. The blue lines define the areas of space covered by one experimental pattern (eo) exposed during crystal rotation. The blue arcs with arrows show the angular range covered by the experimental figure. The diagram shows three such experimental patterns. Several (in FIG. 2) experimental patterns are always combined into one virtual frames (in, shown in the diagram by red arcs with arrows).

The obtained data were further processed by the computer program PETS2 (<http://pets.fzu.cz>). Data processing included these steps: (for more details see e.g. Palatinus, L., Brazda, P., Jelinek, M., Hrda, J., Steciuk, G. & Klementova, M. (2019) *Specifics of the data processing of precession electron diffraction tomography data and their implementation in the PETS2.0 program, Acta Cryst.* B75, 512-522):

finding maxima in all diffraction patterns and determining their coordinates in reciprocal space (see FIG. 1);

determining orientation matrix, i.e. finding the parameters of the crystal lattice and determining the orientation of the crystal in space. The determined lattice parameters were a=18.273 Å, b=18.646 Å, c=6.617 Å, α=90°, β=90°, γ=90°;

determining diffracted intensities of all potentially excited reciprocal lattice points on all experimental diffraction patterns (see FIG. 1);

creating virtual diffraction frames, whereby:
- one virtual frame covered an angular range of 1.2° and was thus created by combining two experimental diffraction patterns (see FIG. 2);
- all points of the reciprocal lattice that were within the angular range covered by the virtual diffraction frame were found.
- for each point of the reciprocal lattice found, all diffraction intensities belonging to this point were summed on all experimental diffraction patterns.
- the list of intensities thus obtained belonging to the points of the reciprocal lattice forms a data set called the virtual diffraction frame.
- the orientation of the virtual diffraction frame was determined as the average of the orientations of the two experimental diffraction patterns that make it up.
- each subsequent virtual diffraction frame was shifted by one experimental diffraction pattern compared to the previous one. Thus, the angular overlap of two consecutive virtual diffraction frames was 0.6°.
- the result of the whole procedure was a list of 48847 reflections on 165 virtual diffraction frames.

The output from the PETS program in the form of a list of reflections with their indices, intensities and standard deviations was further processed by the Jana2006 program (<http://jana.fzu.cz>) in order to find and refine the crystal structure model. This method involved the following steps:
- finding an approximate structure model containing a list of atoms in the structure with their approximate positions
- refinement of the structure model by the least squares method, while the dynamical diffraction theory was used to calculate the theoretical diffracted intensities needed for the refinement. The refinement resulted in residual factors $R_1=0.0947$, $wR_2=0.0968$.
- determining correct absolute structure that included the following steps:
  - creating an inverted structure model, i.e. a model in which the coordinates of all atoms in the structure have been replaced by coordinates with the same absolute value and opposite sign;
  - refining of the structure model in the same way as the refinement of the previous model.
  - refining the inverted model resulted in residual factors $R_1=0.1559$, $wR_2=0.1663$. Because these values are more than 0.01 higher than the values for the non-inverted model, this procedure clearly determines that the original, non-inverted model corresponds to the correct absolute structure.

The resulting refined structure model was compared with the known reference structure of natrolite determined by X-ray single crystal diffraction. The average difference in interatomic distances was 0.0125 Å.

Abiraterone Acetate

Figure 7:
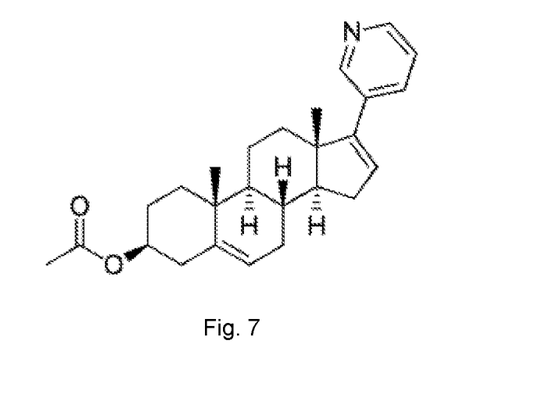
FIG. 7 shows the structure formula of the abiraterone acetate molecule.

Abiraterone acetate is an organic substance with pharmaceutical effects. Its chemical formula is $C_{26}H_{33}NO_2$. The abiraterone acetate molecule is shown in FIG. 7. The molecule is chiral and crystallizes in the $P2_12_12_1$ space group, which means that it makes sense to determine the absolute structure of this material.

The white powder of abiraterone acetate was dissolved in distilled water. After one minute, a drop of the solution was dropped on a carbon-coated copper grid. This grating was placed in a sample holder for a transmission electron microscope with cooling capability and placed in a FEI Tecnai G2 20 microscope with an accelerating voltage of 200 kV, with an $LaB_6$ electron source and equipped with a SIS Veleta CCD detector. The sample was cooled to 100 K.

Data acquisition took place as follows:

By examining the crystals and visually inspecting their diffraction pattern, suitable crystals were selected for measurement. In total of five crystals were selected for measurement and further processing. For the first crystal, the goniometer with the crystal was rotated to the −28.3° position. The crystal was then rotated 0.4° the angular speed of 0.465° per second and its diffraction pattern was recorded on a detector throughout the rotation. The resulting experimental diffraction pattern was saved on a computer hard disk. This diffraction pattern procedure was repeated for another 0.4° rotation. The total rotation of the crystal was 80°, so that a total of 200 experimental diffraction patterns were obtained.

The same procedure was repeated for the other four crystals. The rotational speed and angular range of rotation for one experimental diffraction pattern remained the same. The total range of rotation was 87.2°, 78.4°, 50.4°, and 54.0° for crystals 2, 3, 4 and 5, respectively.

The data obtained from each crystal separately were further processed by the computer program PETS2 (<http://pets.fzu.cz>). Data processing included these steps (for more details see e.g. Palatinus, L., Brazda, P., Jelinek, M., Hrda, J., Steciuk, G. & Klementova, M. (2019) *Specifics of the data processing of precession electron diffraction tomography data and their implementation in the PETS2.0 program, Acta Cryst.* B75, 512-522):
- finding maxima in all diffraction patterns and determining their coordinates in reciprocal space (see FIG. 1);
- determining orientation matrix, i.e. finding the parameters of the crystal lattice and determining the orientation of the crystal in space. The determined lattice parameters were a=7.470 Å, b=9.689 Å, c=30.20 Å, $\alpha=89.96°$, $\beta=89.98°$, $\gamma=89.99°$;
- determining diffraction intensities of all potentially excited reciprocal lattice points on all experimental diffraction patterns (see FIG. 1);
- creating of virtual diffraction frames, whereby:
  - one virtual frame covered an angular range of 2° and was thus created by a combination of five experimental diffraction patterns (see FIG. 2);
  - all points of the reciprocal lattice that were within the angular range covered by the virtual diffraction frame were found.
  - for each reciprocal lattice point found, all diffraction intensities belonging to this point were summed on all experimental diffraction patterns.
  - the list of intensities thus obtained belonging to the points of the reciprocal lattice forms a data set called the virtual diffraction frame.
  - the orientation of the virtual diffraction frame was determined as the average of the orientations of all five experimental diffraction patterns that make it up.
  - each subsequent virtual diffraction frame was shifted from the previous one by two experimental diffraction patterns for crystals 1, 2 and 3, and by three experimental diffraction patterns for crystals 4 and 5. The angular overlap of two consecutive diffraction patterns was thus 1.2° and 0.8°, respectively.
  - the result of the whole procedure was a list of 10957 reflections on 285 virtual diffraction frames.

The output from the PETS program in the form of a list of reflections with their indices, intensities and standard deviations is further processed by the Jana2006 program (<http://jana.fzu.cz>) in order to find and refine the crystal structure model. All data were read together and the structure model was refined against the data from all five crystals. This method involved the following steps:

finding an approximate structure model containing a list of atoms in the structure with their approximate positions Refining the structure model by the least squares method, while the dynamical diffraction theory was used to calculate the theoretical diffracted intensities needed for the refinement. The refinement resulted in residual factors $R_1=0.1242$, $wR_2=0.1354$.

Determine the correct absolute structure that included the following steps:

creating an inverted structure model, i.e. a model in which the coordinates of all atoms in the structure have been replaced by coordinates with the same absolute value and opposite sign;

refining the structure model in the same way as the refinement of the previous model.

The refinement of the inverted model resulted in residual factors $R_1=0.1560$, $wR_2=0.1721$. Because these values are more than 0.01 higher than the values for the non-inverted model, this procedure clearly determines that the original, non-inverted model corresponds to the correct absolute structure.

The resulting refined structure model was compared with the known reference structure of abiraterone acetate determined by X-ray single crystal diffraction. The average difference in interatomic distances was 0.0493 Å.

INDUSTRIAL APPLICABILITY

The present invention finds application in the field of computational crystallography. More accurately, the present invention can be applied to both the determination of the crystal structure of inorganic crystals and the structure of organic crystals, and knowledge of the crystal structure can be used in a number of fields, such as metallurgy or the pharmaceutical industry.

What is claimed is:

1. A method for determining a crystal structure model for a crystal, wherein the crystal is capable of electron diffraction, comprising steps:

obtaining electron diffraction data from the crystal by three-dimensional electron diffraction, wherein the data comprises information on crystal diffraction patterns, wherein each diffraction pattern comprises information on scattered electron intensities in each direction and crystal orientation to an incident electron beam during data acquisition, wherein the crystal is rotating or tilting during recording of the diffraction data; and processing the data determining crystal lattice parameters, crystal orientation at the time of diffraction pattern acquisition, indices of each reflection and the scattered electron intensity of each reflection on each diffraction pattern, thereby producing the processed data;

generating virtual diffraction frames by a computer program, wherein each virtual diffraction frame comprising a list of integrated scattered electron intensities for each direction with summed contributions from diffraction patterns forming one virtual frame, the virtual diffraction frames being formed by calculation from the obtained three-dimensional electron diffraction data;

providing an approximate crystal structure model; and refining the approximate crystal structure model using dynamical diffraction theory, wherein the refining comprising steps:

calculating modeled intensities of scattered electrons using dynamical diffraction theory based on the approximate crystal structure model; and minimizing the difference between experimentally determined scattered electron intensities and modeled intensities, wherein the refined crystal structure model is the model with the smallest deviation.

2. The method for determining a crystal structure model for a crystal according to claim 1, further comprising the steps of:

creating a model of opposite absolute structure to the approximate crystal structure model, thereby creating an inverted model;

refining the approximate crystal structure model using dynamical diffraction theory on the inverted model; and comparing quality indicators of the inverted model and a non-inverted model, wherein a correct structure is the one that leads to the smallest deviation between the diffraction patterns and the data calculated on the basis of the aforementioned steps.

3. The method according to claim 1, wherein the step of obtaining electron diffraction data from the crystal by three-dimensional electron diffraction is a continuous crystal rotation measurement.

4. The method according to claim 1, wherein the step of obtaining electron diffraction data from the crystal by three-dimensional electron diffraction is a crystal rotation in steps.

5. The method according to claim 1, wherein the step minimizing the difference between experimentally determined scattered electron intensities and modeled intensities comprises a least squares calculation.

6. A method for determining the absolute structure of a non-centrosymmetric crystal, wherein the crystal is capable of electron diffraction comprising steps:

obtaining electron diffraction data from the crystal by three-dimensional electron diffraction, wherein the data comprising information on crystal diffraction patterns, wherein each diffraction pattern comprising information on scattered electron intensities in each direction and a crystal orientation to an incident electron beam during data acquisition, wherein the crystal is rotating or tilting during data acquisition; and processing the data determining crystal lattice parameters, crystal orientation at the time of a diffraction pattern acquisition, indices of each reflection and the scattered electron intensity of each reflection on each diffraction pattern, thereby producing the processed data;

generating virtual diffraction frames by a computer program, wherein each virtual diffraction frame comprising a list of integrated scattered electron intensities for each direction with summed contributions from all crystal diffraction patterns forming one virtual frame, the virtual diffraction frames being formed by calculation from the obtained three-dimensional electron diffraction data;

providing an approximate crystal structure model; and calculating quality indicators of the approximate crystal structure model using dynamical diffraction theory to calculate model intensities;

creating a model of opposite absolute structure to a current approximate crystal structure model, thereby creating an inverted crystal structure model;

calculating quality indicators of the inverted crystal structure model using the dynamical diffraction theory to calculate the model intensities; and comparing quality indicators of the inverted and non-inverted models, wherein a correct structure is the one that leads to the smallest deviation between the diffraction patterns and data calculated on the basis of a refined structure model.

7. The method according to claim 6, wherein the step of obtaining electron diffraction data from the crystal by three-dimensional electron diffraction is a continuous crystal rotation measurement.

8. The method according to claim 6, wherein the step of obtaining electron diffraction data from the crystal by three-dimensional electron diffraction is a crystal rotation is in steps.

9. An apparatus for determining a crystal structure model comprising:
an electron source capable of emitting an electron beam;
a crystal holder adapted to perform a rotational or tilting movement with a crystal;
a detector detecting scattered electrons by the crystal, the detector is connected to
a data storage and processing unit, wherein:
the processing unit is adapted to determine crystal lattice parameters, crystal orientation at the time of a diffraction pattern acquisition, indices of each reflection and a scattered electron intensity of each reflection on each diffraction pattern, thereby producing processed data; and
generating virtual diffraction frames by a computer program, wherein each virtual diffraction frame comprising a list of integrated scattered electron intensities for each direction with summed contributions from the scattered electrons forming one virtual frame, the virtual diffraction frames being formed by calculation from a provided three-dimensional electron diffraction data; and wherein
the data storage is configured to provide an approximate crystal structure model or the processing unit is adapted to perform analysis of the processed data leading to obtaining an approximate crystal structure model; and wherein
the processing unit is adapted to refine the approximate crystal structure model.

10. The apparatus according to claim 9, wherein the processing unit is adapted to refine the approximate crystal structure model using dynamical diffraction theory, wherein the processing unit, during the refining, is adapted to:
calculate modeled intensities of scattered electrons using dynamical diffraction theory based on the approximate crystal structure model; and
minimize the difference between experimentally determined scattered electron intensities and modeled intensities, wherein the refined crystal structure model is the model with the smallest deviation.

11. The apparatus according to claim 10, wherein the processing unit is configured to determine the absolute structure of non-centrosymmetric crystals, wherein the processing unit is configured to:
create a virtual model of opposite absolute structure to the structure of the approximate crystal structure model, thereby creating an inverted model;
refine the approximate crystal structure model using the dynamical diffraction theory on the inverted model; and
compare quality indicators of the inverted model and the scattered electrons, wherein a correct absolute structure is the one that leads to the smallest deviation between thereof.

12. The apparatus according to claim 9, wherein the processing unit is adapted to refine the approximate crystal structure model; and wherein the apparatus is adapted to
calculate quality indicators of the refined crystal structure model; and
compare the quality indicators, wherein a correct crystal structure is considered as the modeled crystal structure leading to the smallest deviation between the scattered electrons and data calculated on the basis of the refined crystal structure model.

13. The apparatus according to claim 12, wherein the processing unit is adapted to create a model of opposite crystal structure to the approximate crystal structure model, thereby creating an inverted model; and wherein the step of comparing quality indicators is comparing quality indicators of the inverted model and a non-inverted model, wherein the correct crystal structure is the one that leads to the smallest deviation between experimental data and the data calculated on the basis of the refined crystal structure model.

14. The apparatus according to claim 9, wherein the detector is set to collect data simultaneously with a rotation of the crystal.

15. The apparatus according to claim 9, wherein the detector is set to collect data step by step during a rotation of the crystal.

* * * * *